United States Patent [19]

Trissel

[11] Patent Number: 5,681,846
[45] Date of Patent: Oct. 28, 1997

[54] EXTENDED STABILITY FORMULATIONS FOR PACLITAXEL

[75] Inventor: Lawrence A. Trissel, Houston, Tex.

[73] Assignee: Board of Regents, The University of Texas System, Austin, Tex.

[21] Appl. No.: 406,209

[22] Filed: Mar. 17, 1995

[51] Int. Cl.$^6$ ............... A61K 31/335; A61K 31/34; A61K 9/50; A01N 43/02

[52] U.S. Cl. ............... 514/449; 514/511; 514/529; 514/532; 514/533; 514/534; 514/650; 514/651; 514/656

[58] Field of Search ............... 514/511, 529, 514/532, 533, 534, 650, 651, 656, 449

[56] References Cited

U.S. PATENT DOCUMENTS

| | | | |
|---|---|---|---|
| 5,403,858 | 4/1995 | Bastard et al. | 514/449 |
| 5,438,072 | 8/1995 | Bobee et al. | 514/449 |

OTHER PUBLICATIONS

Alkan–Onyuksel et al., "A Mixed Micellar Formulation Suitable for the parenteral Administration of Taxol," *Pharm. Res.*, 11:206–212, 1994.

Mathew et al., "Synthesis and Evaluation of Some Water–Soluble Prodrugs and Derivatives of Taxol with Antitumor Activity," *J. Med. Chem.*, 35:145–151, 1992.

Nicolaou et al., "Design, synthesis and biological activity of protaxols," *Nature*, 364:464–466, 1993.

Pfeifer and Hale, "Precipitation of paclitaxel during infusion by pump," *Am. J. Hosp. Pharm.*, 50:2518–2521, Dec., 1993.

Rowinsky and Donehower, "The Clinical Pharmacology of Paclitaxel (TAXOL®)," *Seminars in Oncol.*, 20:16–25, Aug., 1993.

Sharma and Straubinger, "Novel Taxol Formulations: Preparation and Characterization of Taxol–Containing Liposomes," *Pharm. Res.*, 11(6):889–896, 1994.

Trissel and Bready, "Turbidimetric assessment of the compatibility of taxol with selected other drugs during simulated Y–site injection," *Am. J. Hosp. Pharm.*, 49:1716–1719, Jul., 1992.

Trissel and Martinez, "Turbidimetric assessment of the compatibility of taxol with 42 other drugs during simulated Y–site injection," *Am. J. Hosp. Pharm.*, 50:300–304, Feb., 1993.

Waugh et al., "Stability, compatibility, and plasticizer extraction of taxol (NSC–125973) injection diluted in infusion solutions and stored in various containers," *Am. J. Hosp. Pharm.*, 48:1520–1524, Jul., 1991.

*Primary Examiner*—Nathan M. Nutter
*Attorney, Agent, or Firm*—Arnold, White & Durkee

[57] ABSTRACT

The present invention is directed to improved pharmaceutical compositions employing paclitaxel that are formulated to increase stability and solubility. These improved formulations are useful in long-term, multi-day continuous infusion protocols, and have the advantage of reducing the number of infusion system breaks during the entire period of drug administration. Also disclosed are kits for use in preparing paclitaxel for long-term infusion and enhanced solubility.

18 Claims, 2 Drawing Sheets

EXTENDED STABILITY FORMULATIONS FOR PACLITAXEL

BACKGROUND OF THE INVENTION

1. Field of the Invention

The present invention relates generally to the fields of cancer therapeutics. More particularly, it concerns formulations of paclitaxel that extend its solubility and stability in solutions, allowing for longer storage and the long-term infusion of paclitaxel over extended time periods.

2. Description of the Related Art

Paclitaxel is a natural compound present in the bark of the Pacific Yew tree (*Taxus brevifolia*) and related species. Paclitaxel has potent anticancer activity, and is currently being commercially marketed by Mead Johnson Oncology as Taxol® for the treatment of ovarian cancer. (Mead Johnson Oncology, 1993). The product is undergoing continued testing by the National Cancer Institute (NCI) and Mead Johnson Oncology in clinical trials for other cancers including breast cancer.

Paclitaxel functions as a mitotic spindle poison and is a potent inhibitor of cell replication in vitro. Paclitaxel markedly enhances all aspects of tubulin polymerization; initiation and elongation are more rapid. As noted above, the drug is marketed for the treatment of ovarian cancer, and, in clinical trials has shown activity against lymphoma, breast cancer, and possibly other tumors.

Because of paclitaxel's poor solubility in water, (Flora et al., 1992) the current clinical formulation is a 6-mg/mL solution of paclitaxel in a vehicle composed of 527 mg of polyoxyethylated castor oil (Cremophor® EL) and 49.7% (v/v) Dehydrated Alcohol, USP, per milliliter. For infusion, this formulation is diluted in either 0.9% Sodium Chloride injection, USP, or 5% Dextrose injection, USP. (Mead Johnson Oncology, 1993). Dilution of the clinical formulation of paclitaxel in intravenous infusion fluids produces a solution that has a slight haze and, occasionally, a few minute particles. Therefore, for prolonged infusions of paclitaxel, it is recommended that an intravenous administration set with a 0.22-μm inline filter be used. (Mead Johnson Oncology, 1993). Further, the formulation is physically unstable, and in aqueous solutions exhibits the formation of paclitaxel precipitate. As a consequence, Mead Johnson Oncology limits the utility time of Taxol® intravenous infusion admixtures to 27 hours. (Mead Johnson Oncology, 1993).

At present, intravenous infusions of paclitaxel are prepared for patient administration within the concentration range of 0.3 to 1.2 mg/mL.[1] In addition to paclitaxel, the final solution for administration consists of solvent concentrations up to ethanol 10%, Cremophor® EL 10%, and aqueous solution 80%. The short (27-hour) physical stability of the paclitaxel admixtures has been adequate for short-term infusions. Newer clinical procedures, however, requiring that paclitaxel be administered over extended time periods as a continuous infusion, are problematic for both patients and care givers. While Cremophor® EL has been used to solubilize Cyclosporine (650 mg/ml), miconazole (0.115 mg/ml) and phytonadione (70 mg/ml) (Trissel, 1994), it is problematic for long-term treatment protocols.

An undesirable effect of Cremophor® EL in paclitaxel and other drug formulations is the production of occasional anaphylactoid reaction with dyspnea, hypotension, angioedema, and urticaria. These undesirable adverse effects were encountered in clinical trials, and in at least one case, the reaction was fatal.

Initial attempts to alleviate the physical stability problem of paclitaxel by increasing the amount of Cremophor® EL in the formulation leads to greater physical stability, but may also lead to an increased in the incidence of adverse anaphylactoid reactions. Ideally, any change to enhance physical stability would not require an increased amount of surfactant.

Other methods to increase the long-term solubility of paclitaxel have been attempted. For example, common, water-miscible cosolvents are used as a method of formulating intravenous non-water-soluble drugs. However, often the drugs precipitate upon the addition of the cosolvent mixture to IV fluids or blood, and extremely slow infusions are needed to prevent this precipitation (Yalkowsky, 1977).

Still further methods for increasing paclitaxel solubility while removing the surfactant involves the synthesis of water soluble, chemically stable derivatives of paclitaxel, some of which appear to act as prodrugs (Mathew et al., 1991, Deutsch et al., 1989). Additionally, others have turned to the use of liposome preparations as a means of eliminating surfactant and reducing renal and vehicle toxicity, while allowing greater compatibility with intravenous administration equipment (Sharma et al., 1994).

Recently, several clinical protocols that call for multi-day continuous infusion of paclitaxel have been initiated. Examples include DM93-089 for lymphoid malignancies, DM93-098 for lymphoma, DM-93-101 phase I toxicity and dose seeking study, and DM 93-143 for refractory Hodgkin's disease. The infusion period has usually ranged from 4 to 7 days or even longer. For multi-day continuous infusion, the maximum time recommended by the manufacturer for use of a mixed paclitaxel solution is 27-hours because stability after this time is problematic. A new container must be made each day, and the patient must return to the institution each day to have the bags changed. This is an inconvenience for patients and staff, and increases the cost of the therapy as well. Further, the risk of intravenous catheter microbial colonization is increased with each break of the infusion system to change bags. To minimize the inconvenience, cost, and problems associated with multiple infusion system breaks, it becomes advantageous to have a product that remains stable for the entire period of the multi-day administration.

Thus, the present inventor determined that there exists a strong need for a formulation of paclitaxel that is stable for long periods of time and that does not induce new or more intense negative side effects to patients.

SUMMARY OF THE INVENTION

The present invention seeks to overcome the drawbacks inherent in the prior art by providing new compositions and methods for use in long-term infusion of paclitaxel. Current formulations of paclitaxel precipitate from solution after a period of approximately 3 to 5 days and as a consequence, the inventor developed formulation modifications that would lead to extended physical stability of paclitaxel in solution. The inventor has discovered novel formulations combining paclitaxel, a surfactant and dehydrated alcohol unexpectedly extending the stability and solubility of taxol in solution for greater periods of time to allow the use of a single solution for IV administration.

The present inventor developed methods that increase the solubility time in solution for paclitaxel by increasing the concentration of a solvent, such as dehydrated alcohol, relative to the amount of surfactant. Moreover, the inventor has further shown that decreasing the concentration of paclitaxel relative to the surfactant increases the solubility time. Studies by the inventor have generally shown that by selectively increasing the alcohol concentration or decreasing the surfactant concentration in the formulation relative to the paclitaxel, significant increases in the solubility times of paclitaxel are achieved.

In part, the present invention provides a delivery system for paclitaxel to a patient that is characterized by 1) avoidance of solubility problems of paclitaxel, 2) improved paclitaxel stability, 3) avoidance of the increased risk of anaphylactoid reactions and cardiotoxicity, 4) ability to administer paclitaxel as a continuous infusion longer that 27 hours, without the need to change to a freshly made batch of the drug, 5) increased therapeutic efficacy of paclitaxel, and 6) modulation of multidrug resistance in cancer cells.

The present invention increases the stability of paclitaxel in solutions when diluted to concentrations that may be used clinically in 0.9% Sodium Chloride Injection, USP, and 5% Dextrose Injection, USP, and stored in various types of containers. As used herein, "paclitaxel" or "an antineoplastic derivative thereof" is intended to include paclitaxel or any derivatives of paclitaxel that are used in cancer chemotherapy. In the examples described herein, the percentages of solvent, solubilizer, and preservative are based on the standard vial of paclitaxel available from the manufacturer, at a concentration of 6 mg/ml. It is recognized that other concentrations of paclitaxel may be utilized within the scope of the present invention, using the proportions of solvent and surfactant described herein. Moreover, other clinically useful diluents in addition to 0.9% sodium chloride and 5% dextrose are also contemplated to be within the scope of the present invention.

Paclitaxel is supplied by the manufacturer as a concentrate at 6 mg/mL in a solvent mixture composed of Cremophor® EL surfactant, 527 mg/mL and dehydrated alcohol, USP, 49.7% (v/v). (Mead Johnson Oncology, 1993). The present inventor has discovered that the stability of the paclitaxel in solution may be increased if the paclitaxel concentration is reduced from 6 mg/ml to 3 mg/ml, while maintaining the solvent concentration at about 50% and the surfactant percentage at about 50%. Suitable lower ranges of paclitaxel are about 1 mg/ml, or about 2 mg/ml, or about 3 mg/ml. Suitable upper ranges of paclitaxel are about 36 mg/ml, about 24 mg/ml, about 15 mg/ml, about 10 mg/ml, about 5 mg/ml, about 4 mg/ml or about 3.5 mg/ml. As used herein, "increased stability" means a paclitaxel preparation that may be administered to a patient that remains in solution for periods greater than 27 hours.

Suitable surfactants for use with the present invention include nonionic agents, such as long-chain fatty acids and their water-insoluble derivatives. These include fatty alcohols such as lauryl cetyl and stearyl alcohol, glyceryl esters such as the naturally occurring mono-, di- and triglycerides, and fatty acid esters of fatty alcohols, such as propylene glycol, polyethylene glycol, sorbitan, sucrose and cholesterol. Also useful are compounds that are those that have polyoxyethylene groups added through an ether linkage with an alcohol group. Compounds that are particularly useful in the present invention include the polyoxyethylene sorbitan fatty acid esters and polyoxyethylene glycerol and steroidal esters.

Cremophor® EL is a polyoxyethylated castor oil surfactant. It is combined with dehydrated ethanol 1:1 as the vehicle for paclitaxel. It has been found that the amount of Cremophor® EL required to deliver the necessary doses of paclitaxel is higher than that administered with any other marketed drug. This vehicle has been observed to cause serious, life-threatening anaphylactoid reactions in animals and humans, and is physically incompatible with some intravenous infusion sets and solution containers. A feature of the present invention is to increase the length of time paclitaxel remains in solution without increasing the amount of surfactant, such as Cremophor, administered to the patient.

In certain embodiments, the lower amount of surfactant is between about 5%, or about 10%, or about 20%, or about 30%, or the total volume. Upper levels of surfactant are typically about 35%, or about 40%, about 50%, or about 60% of the total volume. In certain embodiments, the surfactant concentration is about 25% of the total volume.

It is contemplated that other surfactants may be used to solubilize paclitaxel. For example, it is contemplated that polysorbate 80 may be useful, since this surfactant has been used in the solubilization of Alteplase (0.008 to 0.011%) Chlordiazepoxide HCl (4%), Etoposide (80 mg/ml), and Vitamin A injection (12%). Additionally, Polysorbate 20, sodium laurate, sodium oleate, and sorbitan monooleate are likely to be useful in context of the present invention. Anionic surfactants may also be useful in the practice of the present invention. Examples of these include, but are not limited to, sodium cholate, sodium laruyl sulfate, sodium deoxycholate, sodium laurate, soduim oleate, or potassium laurate In certain embodiments, dehydrated ethanol is used as a solvent in paclitaxel preparations. In other embodiments, glycols such as propylene glycol or polyethylene glycol are within the scope of the invention. For example, propylene glycol has been used as a solvent for chlordiazepoxide, diazepam, digoxin and pentobarbital sodium. Polyethylene glycol is useful as a solvent for etoposide, lorazepam and secobarbital. (Trissel, 1994). It is recognized that the determination of a proper concentration of glycol to fully solubilize the paclitaxel is within the scope of a skilled artisan, and would not require undue experimentation. (Avis, 1986, Motoal and Agharkar, 1984; DeLuca and Boylan, 1984; Avis, 1990).

It is further contemplated that simple complex polyols may be suitable solvents. Moreover, the use of non-dehydrated alcohols is suitable within the scope of the present invention, up to approximately 90% of the total volume.

In certain aspects of the invention, the lower amount of solvent is between about 12%, or about 15%, or about 20%, or about 25%, or about 30%, or about 35%, or about 40%, or about 50% of the total volume. In other aspects, the upper amount of alcohol is about 55%, or about 60%, or about 70%, or about 85%, or about 90% of the total volume. In yet other aspects, the alcohol concentration is about 75% of the total volume.

Due to the possibility of microbial contamination, a problem that may be manifest during long-term infusion, the invention also contemplates the use of antimicrobial preservatives in pharmacological amounts to allow infusion into humans. In this regard, the amount of a suitable preservative, for example, benzyl alcohol, is present at between about 0.5% and about 1.5%. Lower concentrations are about 0.5%, about 0.75% and about 0.85%. Upper concentrations range from about 1.5%, about 1.3%, and about 1.0%. An exemplary concentration is about 0.9%. It is recognized that other antimicrobial preservatives may be employed in the present invention, for example phenol, m-cresol, and paraben®.

In related embodiments, the present invention contemplates the preparation of kits that may be employed in the clinic for the accurate mixing of paclitaxel prior to patient administration. Generally speaking, kits in accordance with the present invention may include a suitable vial containing paclitaxel, a dehydrated alcohol or other solvent, and a preservative such that they may be mixed with the contents of a vial of paclitaxel to achieve the percentages and concentrations suitable for long-term infusion. Examples of suitable percentages that yield formulations suitable for maintaining paclitaxel in solution for include, but are not limited to, those set forth in Formulas I, II, and III. It is recognized that these percentages and concentrations serve as representative examples, and that modifications of these formulas by a skilled artisan in accordance with the procedures and guidance set forth herein to achieve similar results is within the scope of the instant invention.

The kit may generally include a vial into which, for example, the paclitaxel, surfactant, dehydrated alcohol, or a preservative may be placed, and preferably suitably aliquotted. The kits of the present invention may also typically include a means for containing the paclitaxel, surfactant, dehydrated alcohol, and preservative containers in close confinement for commercial sale. Such containers may include injection or blow-molded plastic containers into which the desired vials are retained and/or cardboard cartons with cardboard or foam cushioning.

Certain reagents comprising the kit may be provided as liquid solutions, or as a dried powder. When the reagent provided is a dry powder, the powder may be reconstituted by the addition of a suitable solvent, which solvent may be provided.

In alternative embodiments, the kits may include containers of paclitaxel pre-formulated in the concentrations of surfactant and solvent suitable for extended stability and ready for dilution with, for example, 0.9% sodium chloride. Following this mixing, the solutions are then ready for infusion into a patient. It is recognized that solutions prepared in this manner may also include a suitable preservative. Suitable concentrations of solvent include about 90% to about 80% to about 70% to about 60% of the total volume, and the concentrations of surfactant include about It is further contemplated that the extended stability paclitaxel solution may be supplied as a solution ready to infuse in a patient. In such an embodiment, the infusion container holds paclitaxel with sufficient amounts of alcohol and surfactant to yield an extended stability solution, and sufficient amounts of an infusion solution, such as normal saline (0.9% NaCl), or 5% dextrose (D5W). It is envisioned that infusion solutions with 0.9% NaCl or 5% D5W could be provided with alcohol concentrations ranging from about 10% to about 50%, and a surfactant (such as Cremophor EL®) present at about 5% to about 10%. The alcohol or other suitable solvent may be present in the final infusion solution at about 10% to about 50% of the total volume. In certain embodiments, paclitaxel may be supplied at an about 1 mg/ml concentration with about 30% solvent, such as dehydrated ethanol, and about 8%, or about 5%, or about 3% surfactant (for example Cremophor EL®). These solutions may also contain a preservative such as about 0.9% benzyl alcohol.

It is also recognized that paclitaxel may be supplied as a dry powder instead of being admixed with solvent and surfactant. Prepared in this form, the paclitaxel may be a supplied as a dry fill, lyophilized or vacuum-dried from solvent product. Alternatively, paclitaxel could be supplied as a concentrated liquid, dissolved in a solvent that may be, for example, dehydrated alcohol. In this manner, paclitaxel could be supplied in concentrations up to its maximum solubility. Any such concentration range could be supplied up to the maximum solubility of paclitaxel. In certain embodiments, the paclitaxel concentrations may be multiples of the supplied concentration of 6 mg/ml. In other embodiments, the range may be up to 24 or 36 mg/ml. A separate vial of diluent, either surfactant alone or an alcohol/surfactant combination could be used to dilute the paclitaxel concentrate or to add to the aqueous infusion solution to establish the proper alcohol/solvent/surfactant conditions prior to adding the paclitaxel concentrate to the infusion solution.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1A:
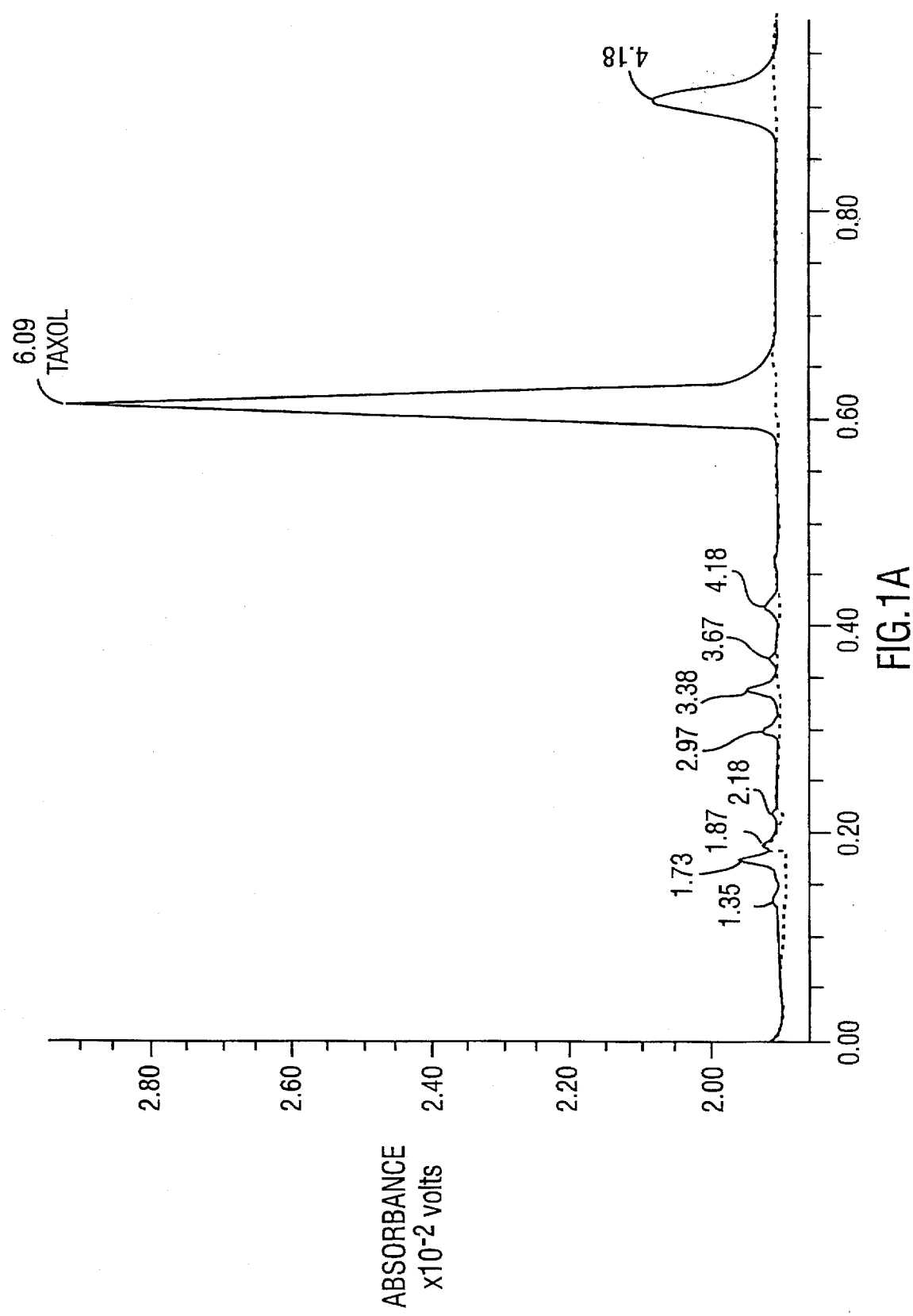
FIGS. 1(a) and 1(b) (a) HPLC tracing of paclitaxel performed at 254 nm. (b) Accelerated paclitaxel decomposition measured following pH adjustment of a paclitaxel solution to 11.14 and a one hour wait at room temperature.

The present invention discloses novel formulations of paclitaxel that increase its stability and maintain solubility for extended periods of time in solution.

The paclitaxel extended stability injection of the present invention is a modified formulation of the commercial product Taxol® (Mead Johnson Oncology, Div. Bristol-Myers Squibb) designed to increase the utility time of paclitaxel in infusion solutions before the drug begins to precipitate (see, for example, Formulas I and II in Table I).

Paclitaxel is very insoluble in aqueous media. (Flora et al., 1992). Consequently, the commercial injection is formulated as a concentrate at 6 mg/mL in a solvent mixture composed of Cremophor® EL surfactant 527 mg/mL and dehydrated alcohol, USP, 49.7% (v/v). (Mead Johnson Oncology, 1993). For administration the dose is admixed in 5% Dextrose Injection, USP, or 0.9% Sodium Chloride Injection, USP, to a concentration between 0.3 and 1.2 mg/mL. The official labeling (Mead Johnson Oncology, 1993) cites a maximum stability time of 27 hours from preparation. This is brief but adequate for one-day infusion.

A solution stability study of the current commercial formulation was conducted (Formula IV, Table I), and showed that while paclitaxel is chemically stable, it begins to crystalize out of solution after 3 to 5 days, rendering it unsuitable for continued parenteral administration. To allow for preparation time (usually about 4 hours) and adequate safety for the potentially erratic precipitation phenomenon, a maximum infusion time of 48 hours is being used based on these data.

Consequently, the inventor developed modified formulations of paclitaxel designed to keep paclitaxel dispersed for a minimum of seven days. The approach included increasing the solvent content relative to the drug in the vial, and combining this with admixing high concentrations of paclitaxel (and associated solvent) in infusion solutions for slow infusion. The paclitaxel thus remains dispersed in solution for long periods of time.

A study of each formula in 5% Dextrose injection, USP, showed considerable extension of the time to precipitation.

For example, Formulas I & II exhibited precipitation after two weeks while Formula III has remained in solution for greater than one year. Presented in Table I are representative paclitaxel formulations of the present invention (Formulas I, II, III, and the commercially available formulation (Formula IV)). It is recognized that the present invention is not limited to these formulas, which are representative of the combinations of solvent and surfactant percentages, and paclitaxel concentrations for extended paclitaxel stability in infusion solutions.

TABLE I

Representative Formulation Compositions of the Product Concentrates and After Dilution for Administration

|  | Concentrate | Diluted |
|---|---|---|
| Formula I (Extended Stability Formulation) | | |
| Paclitaxel | 3 mg/mL, 10 mL/vial | 1 mg/mL |
| Surfactant | 2.5 mL (25%) | 0.833 mL (8.33%) |
| Alcohol dehydrated | 7.5 mL (75%) | 2.5 mL (25%) |
| Formula II (Extended Stability Formulation with Preservative) | | |
| Paclitaxel | 3 mg/mL, 10 mL/vial | 1 mg/mL |
| Surfactant | 2.5 mL (25%) | 0.833 mL (8.33%) |
| Alcohol dehydrated | 7.23 mL (72.3%) | 2.41 mL (24.1%) |
| Benzyl alcohol | 0.27 mL (2.7%) | 0.09 mL (0.9%) |
| Formula III (Modified Extended Stability Formulation) | | |
| Paclitaxel | 3 mg/mL | 1 mg/mL |
| Surfactant | 5.0 mL (50%) | 16.67 mL (16.67%) |
| Alcohol dehydrated | 5.0 mL (50%) | 16.67 ml (16.67%) |
| Vial Content | 10 mL (30 mg) | |
| Formula IV (Commercial Formulation from Bristol Myers) | | |
| Paclitaxel | 6 mg/mL, 5 mL/vial | 1 mg/mL |
| Cremophor EL ® | 2.5 mL (50%) | 8.33 mL (8.33%) |
| Alcohol dehydrated | 2.5 mL (50%) | 8.33 mL (8.33%) |

*Diluted in 5% Dextrose Injection, USP, or 0.9% sodium chloride injection, USP, to a standard concentration suitable for administration.

Formula I keeps the relative amount of surfactant the same as the current commercial product, which may help with concerns relating to toxicity. A stability study of Formula I at 1 mg/mL in 5% Dextrose Injection, USP, and 0.9% Sodium Chloride Injection, USP, was conducted over 31 days at several temperatures. The paclitaxel was chemically stable as long as it remained in solution. No occurrence of precipitation (including subvisual particles) was found within 14 days in D5W and about 10 days in sodium chloride.

An extended stability formula of paclitaxel could be a product marketed for slow multi-day continuous infusion. The problems encountered in the art with drug precipitation in infusion pumps during infusion within the recommended 27 hours could potentially be alleviated. It is envisioned that other drugs might benefit from this approach including docetaxel (taxotere), and other taxoids, cyclosporine, teniposide, miconazole, and other water-insoluble drugs to increase their stability for multi-day use.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Evaluation of the Alcohol Concentration on the Physical Stability of Paclitaxel Formulations Physical stability testing of extended stability formulations has been evaluated for the effects of changing alcohol concentration on precipitation times in infusion solutions.

Infusion solutions were prepared in 5% dextrose injection, USP, at a paclitaxel concentration of about 1 mg/mL to be used for multiple day continuous infusion. Alcohol concentrations in the final infusion solutions were varied from about 15% to about 50% to simulate variations in potential extended stability paclitaxel formulations.

The current commercial product is labeled for 27 hour stability. It has been found that the drug molecule is chemically stable in solution, but is subject to early precipitation. Crystalline precipitation began in three to five days in some samples and within seven days in most samples. It was determined that the safe stability period in solution was a total of about 52 hours—4 hours for preparation and transportation to the use site and 48 hours for administration.

It has been found that the time to precipitate formation is variable even with the increased alcohol content. Other factors apart from the alcohol content may affect the time to precipitation. Such factors may include the inherent particle content (size, shape, number) that is inevitable in infusion solutions and drug products. Also, the nature of the inner surface of the container and the container material may play a role, with containers having rough spots creating a place for earlier precipitation to begin. All of these other factors are beyond the control of the clinician, which makes the stabilizing effect of an increased alcohol content all the more important.

The present study evaluated in triplicate paclitaxel 1 mg/mL in 5% dextrose injection, USP, with alcohol concentrations ranging from about 15% to about 50% (Table II). In the 15 to 20% range, the time to precipitation varied from about 9 to 14 days in most samples. This is comparable to the 10 to 14 days previously found, and substantially better than the 3 to 5 days for the commercial product. Within the 15 to 20% group, however, the time to precipitation was variable and not linearly related to alcohol content. It is surmised that the approximate 1% alcohol concentration increments studied do not demonstrate a consistent change in paclitaxel solubility within the group. In both this study and the previous studies, paclitaxel solution having alcohol in the 15 to 20% range have not precipitated before 9 days, a time greater than the current commercial preparation.

The 25% alcohol samples showed increased stability (see Table II). The earliest microprecipitation appeared after 14 days in one sample with gross precipitation in 21 days. Additionally, the 30 and 50% alcohol-containing solutions are remarkably more stable. After storage of 60 days, no precipitation, not even microcrystals, have appeared in any sample. While these samples show a much greater stability, the "break point" or step function was achieved at an alcohol concentration of about ≧30%.

TABLE II

Precipitation Times of Paclitaxel 1 mg/mL in 5% Dextrose Injection with Varying Alcohol Concentrations[a]

| Alcohol % | Precipitation Time Days[b] |
|---|---|
| 15 | 14 |
| 16 | 12 |
| 17 | 10 |
| 18 | 12 |
| 19 | 9[c] |
| 20 | 9[c] |
| 25 | 14[d] |
| 30 | >60[e] |
| 50 | >60[e] |

[a]Cremophor ® EL concentration held constant at 8.3%, the same as the current commercial product diluted to 1 mg/mL.
[b]Earliest precipitation among triplicate samples.
[c]One sample precipitated at 9 days, 2 samples at 14 days or more.
[d]One sample did not precipitated after 60 days.
[e]All three samples were still in solution after 60 days.

EXAMPLE 2

Paclitaxel Extended Stability Formula with Antimicrobial Preservative

The Food and Drug Administration is insistent that any infusion solution designed to be administered over periods exceeding 24 hours should be able to pass the USP Antimicrobial Agent Effectiveness test (USPXXII, <51>, p 1478) whether or not antibacterial preservatives are actually present. This arises from concerns about the potential for microbial growth over time if the solutions are inadvertently contaminated during preparation, and is intended to comply with FDA regulations relating to solution sterility for infusion.

For administration of the formulas, the dose is diluted to concentration of about 0.8 to 1.0 mg/mL in 5% Dextrose Injection, USP, or 0.9% Sodium Chloride Injection, USP. A 1.0 mg/mL concentration is made by diluting with twice the volume of Paclitaxel Extended Stability Injection. A suitable intravenous infusion pump is used to assure uniform and constant delivery of this highly-concentrated solution over the required time interval. The fluid volume delivered is much reduced compared to the conventional formulation.

For this testing, each of the three formulations were diluted with 5% Dextrose Injection, USP, to a final paclitaxel concentration of about 1 mg/mL. At this concentration, the formulation may be used in continuous infusion therapy over multiple days utilizing an infusion pump. Formula I is the original proposed extended stability paclitaxel formulation. Formula II is a modification that includes the antimicrobial preservative benzyl alcohol at a concentration that will yield about a 0.9% concentration when diluted in the D5W. For the purposes of this invention, the preservative concentration is nominally at about 0.9%, however it is recognized that any concentration that gives the requisite antimicrobial activity is within the scope of this invention. Thus, the concentration of preservative may range from between about 0.4% to about 1.8%, with the preferred concentration at about 0.9%. Finally, the current commercial formulation of paclitaxel (Taxol®, Bristol Myers) was also evaluated at 1 mg/mL. The actual testing was performed by an independent contractor. Tables III and IV show that both Formula I and II, with and without added preservative, pass the antimicrobial test. It is of importance to note that the commercial product could not be tested due to drug precipitation.

These studies indicate that the extended stability paclitaxel formulation, even without antimicrobial preservative, will be suitable for continuous infusion.

TABLE III

Formula I was used in these studies

Antimicrobial Preservatives Effectiveness Test

METHOD: USP XXII, pp. 1478–1479 (Anon, 1989)
ON TEST: 08/30/1994 OFF TEST: 05/04/1994
RESULTS: Pass

| Organism Time | A. niger | C. albicans | E. coli | P. aeruginosa | S. aureus |
|---|---|---|---|---|---|
| Inoculum per mL Product | 1,000,000 organisms/mL | 420,000 organisms/mL | 340,000 organisms/mL | 300,000 organisms/mL | 450,000 organisms/mL |
| 0 Hr. | 600,000 organisms/mL | 680,000 organisms/mL | 320,000 organisms/mL | 118,000 organisms/mL | 880,000 organisms/mL |
| Week 1 | 1,900 organisms/mL | Less than 10 organisms/mL None Detected | Less than 10 organisms/mL None Detected | Less than 10 organisms/mL None Detected | Less than 10 organisms/mL None Detected |
| Week 2 | 100 organisms/mL | Less than 10 organisms/mL None Detected | Less than 10 organisms/mL None Detected | Less than 10 organisms/mL None Detected | Less than 10 organisms/mL None Detected |
| Week 3 | 130 organisms/mL | Less than 10 organisms/mL None Detected | Less than 10 organisms/mL None Detected | Less than 10 organisms/mL None Detected | Less than 10 organisms/mL None Detected |
| Week 4 | 20 organisms/mL | Less than 10 organisms/mL None Detected | Less than 10 organisms/mL None Detected | Less than 10 organisms/mL None Detected | Less than 10 organisms/mL None Detected |

TABLE IV

Formula II was used in these studies

Antimicrobial Effectiveness Test

METHOD: USP XXII, pp. 1478–1479
ON TEST: 03/30/1994 OFF TEST: 05/04/1994
RESULTS: Pass

| Organism Time | A. niger | C. albicans | E. coli | P. aeruginosa | S. aureus |
|---|---|---|---|---|---|
| Inoculum per mL Product | 1,000,000 organisms/mL | 420,000 organisms/mL | 340,000 organisms/mL | 300,000 organisms/mL | 450,000 organisms/mL |
| 0 Hr. | 600,000 organisms/mL | 490,000 organisms/mL | 74,000 organisms/mL | 11,200 organisms/mL | 500,000 organisms/mL |
| Week 1 | 80 organisms/mL | Less than 10 organisms/mL None Detected | Less than 10 organisms/mL None Detected | Less than 10 organisms/mL None Detected | Less than 10 organisms/mL None Detected |
| Week 2 | 50 organisms/mL | Less than 10 organisms/mL None Detected | Less than 10 organisms/mL None Detected | Less than 10 organisms/mL None Detected | Less than 10 organisms/mL None Detected |
| Week 3 | Less than 10 organisms/mL None Detected | Less than 10 organisms/mL None Detected | Less than 10 organisms/mL None Detected | Less than 10 organisms/mL None Detected | Less than 10 organisms/mL None Detected |
| Week 4 | Less than 10 organisms/mL None Detected | Less than 10 organisms/mL None Detected | Less than 10 organisms/mL None Detected | Less than 10 organisms/mL None Detected | Less than 10 organisms/mL None Detected |

EXAMPLE 3

Evaluation of the Stability of Taxol in Various Solutions

METHODS

Materials.

Paclitaxel injection (Mead Johnson Oncology, Princeton, N.J.) was supplied by the manufacturer. The infusion solutions, 5% dextrose injection (McGaw, Irvine, Calif.) and 0.9% sodium chloride injection (McGaw, Irvine, Calif.), were obtained commercially. Paclitaxel reference standard (Bristol-Myers Squibb, Princeton, N.J.) was used without further purification. The acetonitrile was HPLC grade. The water used was also HPLC grade and was prepared immediately before use.

HPLC Analysis.

Paclitaxel concentrations were determined using a stability-indicating HPLC assay method based on the method of Waugh et al. with modifications to achieve satisfactory chromatography in the inventor's laboratory. The liquid chromatograph consisted of a multisolvent delivery pump (Waters Chromatography, Milford, Mass.), a programmable multiple-wavelength ultraviolet light detector (Waters), a WISP autosampler,(Waters) and a HPLC analytical column (Vydac, Hesperia, Calif.) (250×4.6 mm, 5 µm particle size). The system was controlled and integrated by a personal computer (NEC, Boxborough, Mass.). The mobile phase consisted of 53% acetonitrile in water. The flow rate was 1.5 ml/min and detection was performed at 254 nm. The retention time for paclitaxel was 6.09 minutes (FIG. 1A). Sample aliquots were filtered through 5 µm filter needle. Samples of paclitaxel 1 mg/mL were diluted by a factor of 10 with the respective infusion solution prior to analysis.

Figure 1B:
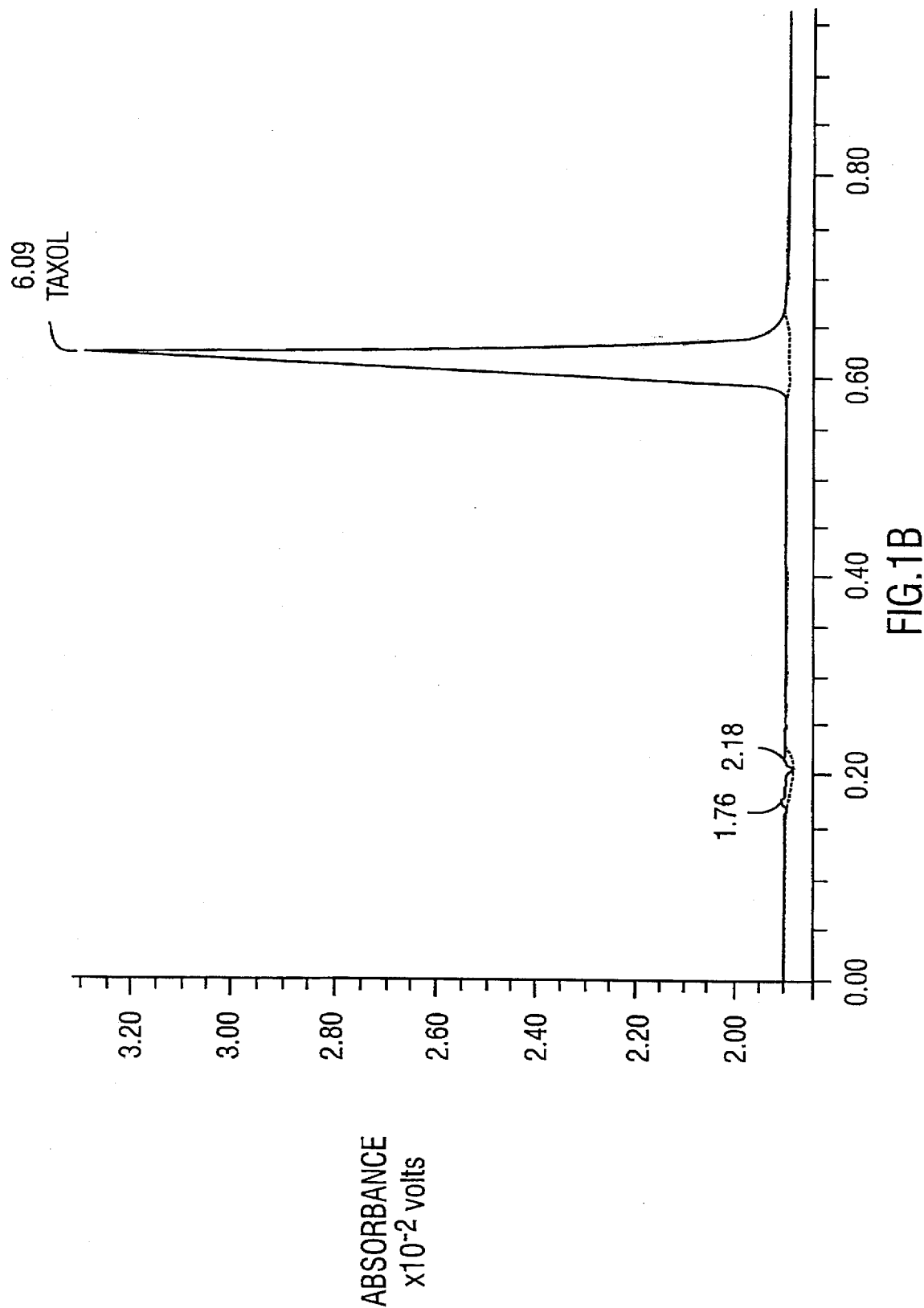

The HPLC analytical method was validated to be stability-indicating by accelerated paclitaxel decomposition. The pH value of a freshly prepared paclitaxel 0.1 mg/mL solution was adjusted to 11.14 with 0.1N sodium hydroxide stock solution. After 1 hr at room temperature, 78% intact paclitaxel remained (FIG. 1B). A major decomposition peak appeared at 9.02 minutes and several small peaks were observed from 2.0 to 4.18 minutes. The decomposition peaks do not interfere with the parent peak. For a nominal 0.1 mg/mL solution of paclitaxel, the mean ±S.D. precision of the assay, determined from 10 replicate injections, was 99.3±0.75 µg/mL. Precision expressed as percent relative standard deviation was 0.76%. Calibration curves were constructed from a linear plot of peak area versus concentration (0.025 to 0.15 mg/mL). The correlation coefficient of the standard curve was greater than 0.9999. The intra-day and inter-day coefficients of variation were 1.4% and 2.0%, respectively.

Triplicate test solutions of paclitaxel 0.1 and 1 mg/mL were prepared both in 5% dextrose injection and 0.9% sodium chloride injection in 150-ml polyolefin minibags and stored statically at 32°, 22°, and 4° C. Aliquots were removed from each bag initially and after 1, 3, 5, and 7 days and stored in 2-ml sterile vials at −70° C. Grossly precipitated solutions were assayed after 31 days of storage. Duplicate HPLC determinations were performed on the aliquots from each test solution.

Physical compatibility was evaluated by visual examination and turbidimetric quantification. Ten-mL samples of each paclitaxel test solution was transferred into colorless 15-mL borosilicate glass screw-cap culture tubes with polypropylene caps. The tubes and caps were triple-washed in high-performance liquid chromatography-grade water and rinsed exteriorly with ethanol. To minimize the effects of scratches and imperfections in the glass, a thin layer of silicone oil was applied to the exterior of the culture tubes.

Visual examination of the samples was performed with the unaided eye in normal laboratory fluorescent light. Samples with no obvious visual incompatibility were further examined using a Tyndall beam (high-intensity monodirectional light source)(Dolan-Jenner, Woburn, Mass.). The test tubes were illuminated from below and viewed at a 90° angle against a dark background to enhance the visibility of small particles.

Turbidimetric assessments of the normally hazy paclitaxel solutions were made using a color-correcting turbidimeter (Hatch, Loveland, Colo.). The turbidimeter was calibrated in the manner described previously (Trissel et al., 1992). Triplicate determinations were made for each sample; the turbidimeter was allowed to return to zero between determinations. Incompatibility has been defined as an increase in turbidity of 0.5 nephelometric turbidity unit (NTU) or more (Trissel et al., 1993). For drug solutions that are normally hazy, such as paclitaxel, a decrease in expected haze may also be evidence of incompatibility (Trissel et al., 1993).

Visual inspections and turbidimetric assessments were performed initially and after 1, 3, 5, 7, 14, and 31 days of storage at each temperature protected from light.

Results and Discussion

When viewed using the Tyndall beam, all samples were initially free of particulate matter but had paclitaxel's normal haze. Turbidity quantification did not result in any change during the study except for samples with noticeable precipitation. Tables V and VI cite the appearance of visually observable precipitation in the samples. Large amounts of white flocculent precipitate appeared after 31 days of storage in many of the samples and after 14 days in a few samples. Precipitation that could be easily seen in the infusion bags with the unaided eye is noted in Tables V and VI.

However, crystalline and needle-like precipitation, only visible using the Tyndall beam, began much earlier. Two samples had small amounts of crystalline precipitate within five days of storage. Most samples had crystalline precipitation within a week. All samples remained compatible in both infusion solutions for at least three days at all three temperatures in these static solutions. It is possible that agitation of the solutions or other factors could reduce the time to precipitate appearance.

The chemical stability of paclitaxel 0.1 and 1 mg/mL in 5% dextrose injection and 0.9% sodium chloride injection are reported in Tables VII and VIII, respectively. Paclitaxel remained chemically stable throughout the study as long a it remained dispersed in the infusion solutions. All assays were above 90% of the initial concentration and most were near 100%. No decomposition products appeared on the HPLC chromatograms. However, losses of around 30 to 50% occurred in samples with gross precipitation.

As indicated by the results, Paclitaxel at 0.1 and 1 mg/mL in 5% dextrose injection and 0.9% sodium chloride injection is chemically stable and physically compatible for three days at 4°, 22°, and 32° C. Precipitation may occur after three days and is the primary limitation on solution utility.

TABLE V

Visual observations of paclitaxel test solution, in 5% dextrose injection.

| Concentration (mg/mL) | Temp. °C. | Storage Time (Days) | | | | |
|---|---|---|---|---|---|---|
| | | 0 | 5 | 7 | 14 | 31 |
| 0.1 | 4 | —[1] | — | — | — | Numerous tiny crystals |
| | 22 | — | — | Tiny crystals and needles | Large amount of crystals, needles, white precipitate | Large amount of crystals, needles, white precipitate[2] |
| | 32 | — | — | Tiny crystals | Crystals, needles, white precipitate | Large amount of crystals, needles, white precipitate |
| 1 | 4 | — | Tiny crystals | Tiny crystals | Crystals, needles, white precipitate | Large amount of crystals, needles, white precipitate |
| | 22 | — | — | Tiny crystals | Crystals, needles, white precipitate | Large amount of crystals, needles, white flocculent precipitate[2] |
| | 32 | — | — | Tiny crystals | Crystals, needles, white precipitate | Large amount of crystals, needles, white flocculent precipitate[2] |

All observations were made using high intensity light enhancement unless stated otherwise. The earliest observed precipitation among triplicate test solutions is reported. All samples were particulate-free at days 1 and 3.
[1]Light blue hazy solution free of particulate matter.
[2]Visible in the infusion solution bag in normal diffuse room light.

TABLE VI

Visual observations of paclitaxel test solutions in 0.9% sodium chloride injection.

| Concentration (mg/mL) | Temp. °C. | Storage Time (Days) | | | | |
|---|---|---|---|---|---|---|
| | | 0 | 5 | 7 | 14 | 31 |
| 0.1 | 4 | —[1] | Tiny crystals | Tiny crystals | Large amount of crystals | Large amount of crystals |
| | 22 | — | — | Tiny crystals | Large amount of crystals | Large amount of crystals, white precipitate |

TABLE VI-continued

Visual observations of paclitaxel test solutions in 0.9% sodium chloride injection.

| Concentration (mg/mL) | Temp. °C. | \multicolumn{5}{c}{Storage Time (Days)} | | | | |
|---|---|---|---|---|---|---|

| Concentration (mg/mL) | Temp. °C. | 0 | 5 | 7 | 14 | 31 |
|---|---|---|---|---|---|---|
| | 32 | — | — | Tiny crystals | Large amount of crystals, white precipitate | Large amount of crystals, white flocculent precipitate[2] |
| 1 | 4 | — | — | Tiny crystals | Large amount of crystals, white precipitate | Large amount of crystals, needles, white flocculent precipitate[2] |
| | 22 | — | — | Tiny crystals | Crystals, needles, white precipitate | Large amount of crystals, needles, white flocculent precipitate[2] |
| | 32 | — | — | Tiny crystals | Tiny crystals | Large amount of crystals, needles, white flocculent precipitate[2] |

All observations were made using high intensity light enhancement unless stated otherwise. The earliest observed precipitation among triplicate test solutions is reported. All samples were particulate-free at days 1 and 3.
[1]Light blue hazy solution free of particulate matter.
[2]Visible in the infusion solution bag in normal diffuse room light.

TABLE VII

Percentage of initial concentration remaining of paclitaxel 0.1 and 1 mg/mL* in 5% dextrose injection, USP.

| Temperature (°C.) | Sample Code | Actual Initial Conc. (µg/ml) | Storage Time (Days) | | | |
|---|---|---|---|---|---|---|
| | | | 1 | 3 | 5 | 7 |
| \multicolumn{7}{l}{Paclitaxel 0.1 mg/mL} | | | | | | |
| 4 | 1 | 102.1 | 99.6 | 100.1 | 100.0 | 100.0 |
| | | 100.8 | 100.6 | 100.6 | 101.7 | 100.3 |
| | 2 | 101.3 | 99.6 | 100.2 | 99.8 | 99.9 |
| | | 102.1 | 100.8 | 100.4 | 100.3 | 100.0 |
| | 3 | 101.1 | 100.3 | 100.0 | 99.6 | 100.5 |
| | | 101.4 | 101.4 | 101.1 | 101.4 | 101.4 |
| 22 | 4 | 100.1 | 99.8 | 99.3 | 99.1 | 100.1 |
| | | 100.8 | 100.4 | 99.1 | 99.8 | 101.1 |
| | 5 | 100.3 | 100.6 | 100.8 | 101.1 | 99.6 |
| | | 99.4 | 100.5 | 101.7 | 100.9 | 100.6 |
| | 6 | 100.5 | 99.1 | 99.1 | 99.4 | 99.3 |
| | | 102.2 | 99.1 | 100.4 | 99.2 | 99.9 |
| | 7 | 106.6 | 98.9 | 98.9 | 98.7 | 100.4 |
| | | 106.8 | 100.9 | 99.3 | 99.2 | 99.7 |
| | 8 | 104.4 | 100.6 | 100.2 | 100.3 | 99.4 |
| | | 106.3 | 100.7 | 100.5 | 100.1 | 101.2 |
| | 9 | 106.0 | 98.4 | 99.1 | 99.8 | 99.5 |
| | | 105.4 | 99.5 | 100.4 | 99.7 | 100.0 |
| \multicolumn{7}{l}{Paclitaxel 1 mg/mL} | | | | | | |
| 4 | 1 | 95.5 | 98.6 | 98.9 | 99.1 | 99.3 |
| | | 96.9 | 99.7 | 99.1 | 99.2 | 99.0 |
| | 2 | 94.2 | 101.4 | 99.9 | 99.0 | 99.9 |
| | | 94.4 | 100.4 | 99.9 | 99.0 | 100.0 |
| | 3 | 95.9 | 100.6 | 100.3 | 100.1 | 99.7 |
| | | 95.9 | 101.2 | 101.0 | 100.2 | 99.7 |
| 22 | 4 | 96.0 | 99.2 | 100.3 | 99.8 | 99.2 |
| | | 96.2 | 99.3 | 100.3 | 99.8 | 98.4 |
| | 5 | 98.3 | 97.8 | 100.1 | 98.1 | 100.1 |
| | | 98.6 | 98.4 | 99.4 | 98.2 | 100.3 |
| | 6 | 100.9 | 98.3 | 99.1 | 99.2 | 99.7 |
| 32 | 7 | 100.9 | 99.3 | 100.0 | 99.8 | 99.1 |
| | | 101.3 | 98.9 | 99.7 | 100.0 | 100.8 |
| | | 101.0 | 99.6 | 98.8 | 99.5 | 100.7 |
| | 8 | 99.7 | 100.4 | 100.0 | 100.1 | 99.4 |
| | | 99.4 | 100.2 | 100.4 | 101.2 | 98.6 |
| | 9 | 98.5 | 100.6 | 99.4 | 100.3 | 100.0 |
| | | 99.3 | 100.3 | 100.1 | 100.5 | 100.6 |

*Nominal concentration.

TABLE VIII

Percentage of initial concentration remaining of paclitaxel 0.1 and 1 mg/mL* in 0.9% sodium chloride injection, USP.

| Temperature (°C.) | Sample Code | Initial Conc. (µg/ml) | Storage Time (Days) | | | |
|---|---|---|---|---|---|---|
| | | | 1 | 3 | 5 | 7 |
| Paclitaxel | 1 | 101.3 | 99.5 | 100.0 | 99.8 | 98.7 |
| | | 101.0 | 99.5 | 99.5 | 99.8 | 99.6 |
| 4 | 2 | 110.3 | 99.2 | 100.6 | 100.0 | 99.9 |
| | | 100.0 | 100.7 | 101.8 | 100.3 | 101.1 |
| | 3 | 100.4 | 99.6 | 100.2 | 99.7 | 100.1 |
| | | 100.4 | 99.4 | 98.9 | 98.5 | 100.1 |
| 22 | 4 | 100.8 | 100.2 | 100.3 | 100.6 | 99.9 |
| | | 100.0 | 99.8 | 100.7 | 100.6 | 100.6 |
| | 5 | 102.3 | 99.6 | 99.3 | 99.1 | 99.6 |
| | | 103.0 | 100.6 | 99.8 | 99.5 | 100.1 |
| | 6 | 103.2 | 100.1 | 100.0 | 98.9 | 99.4 |
| | | 102.9 | 100.0 | 100.6 | 99.6 | 99.8 |

TABLE VIII-continued

Percentage of initial concentration remaining of paclitaxel 0.1 and 1 mg/mL* in 0.9% sodium chloride injection, USP.

| Temperature (°C.) | Sample Code | Initial Conc. (µg/ml) | Storage Time (Days) | | | |
|---|---|---|---|---|---|---|
| | | | 1 | 3 | 5 | 7 |
| 32 | 7 | 102.0 | 101.0 | 100.9 | 100.1 | 101.5 |
| | | 102.1 | 100.4 | 101.3 | 101.7 | 99.5 |
| | 8 | 104.4 | 100.1 | 100.7 | 99.4 | 100.2 |
| | | 104.8 | 100.7 | 100.1 | 100.1 | 100.0 |
| | 9 | 102.1 | 99.5 | 99.8 | 99.5 | 98.0 |
| | | 101.6 | 100.8 | 98.2 | 98.2 | 99.0 |
| 4 | 1 | 99.7 | 101.3 | 99,.8 | 99.1 | 98.7 |
| | | 100.2 | 101.3 | 99.6 | 97.9 | 98.2 |
| | 2 | 99.5 | 97.5 | 98.8 | 98.4 | 97.1 |
| | | 99.5 | 96.7 | 98.7 | 96.4 | 94.7 |
| | 3 | 98.5 | 97.8 | 99.0 | 96.0 | 97.3 |
| | | 98.2 | 97.9 | 98.6 | 95.8 | 96.2 |
| 22 | 4 | 95.5 | 97.9 | 99.2 | 101.3 | 100.6 |
| | | 94.8 | 100.0 | 98.8 | 98.2 | 98.0 |
| | 5 | 97.1 | 97.5 | 97.1 | 98.7 | 98.7 |
| | | 97.0 | 97.8 | 99.0 | 97.4 | 98.8 |
| | 6 | 96.1 | 99.5 | 99.0 | 99.4 | 98.8 |
| | | 96.3 | 98.1 | 98.6 | 98.4 | |
| 32 | 7 | 97.3 | 99.9 | 100.4 | 99.2 | 99.9 |
| | | 97.0 | 100.3 | 101.0 | 99.3 | 100.3 |
| | 8 | 98.2 | 99.7 | 99.8 | 100.1 | 100.1 |
| | | 97.5 | 99.3 | 99.4 | 100.2 | 100.4 |
| 5 | 9 | 98.0 | 100.3 | 100.2 | 100.6 | 100.9 |
| | | 97.7 | 99.7 | 100.4 | 101.1 | 100.5 |

The Paclitaxel Extended Stability Concentrate for Infusion would require dilution to a concentration of about 1 mg/mL in 5% Dextrose Injection, USP, or 0.9% Sodium Chloride Injection, USP. A suitable intravenous infusion pump would be used to assure uniform and constant delivery over extended periods.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alkan-Onyuksel, H., Ramakrishnan, S., Chai, H-B, and Pezzuto, J. M., Pharm. Res. vol 11, pp 206–212 (1994).

Anon. The United States pharmacopeia 22 and the national formulary 17. Rockville, Md: The United States Pharmacopeial Convention, pp. 1478–1479, 1989.

Avis, K. E., Parenteral preparations. In: Remington's pharmaceutical sciences, 18th ed., Gennarro, A. R., Medwick, T., Chase, G. D., et al., eds. Easton Pennsylvania: Mack Publishing Company, pp. 1545–1569, 1990.

Avis, K. E., Sterile products. In: Lacman L. Lieberman, H. A., Kanig, J. L., eds. The theory and practice of industrial pharmacy. Philadelphia: Lea and Febiger, pp. 639–677 (1986).

DeLuca, P. P., Boylan, J. C., Formulation of small volume parenterals. In: Avis, K. E., Lachman, L., Lieberman, H. A., eds. Pharmaceutical dosage forms: parenteral medications, vol. 1, New York: Marcel Dekker, pp. 139–201 (1984).

Deutsch, H. M., Glinski, J. A., Hernandez, M., Haugwitz, R. D., Narayanan, V. L., Suffness, M., and Zalkow, L. H., J.Med. Chem. vol 32, pp 788–792 (1989).

Flora, K. P., et al., NCI investigational drugs chemical information. Bethesda, Md.: National Cancer Institute, pp. 218 (1992).

Grem, J. L., Tutsch, K. D., Simon, K. J., Albertti, D. B., Willson, J. K. V., Tormey, D. C., Swaminathan, S., and Trump, D. L. Cancer Treat. Rep. vol 71, pp 1179–1184 (1987).

Mathew, A. E., Mejillano, M. R., Nath, J. P., Himes, R. H., and Stella, V. J., J. Med. Chem. vol. 35, pp 145–151 (1992).

Mead Johnson Oncology. Taxol package insert. Princeton, N.J. 1993 April.

Motoal, S., Agharkar, S. Preformulation research of parenteral medications. In: Avis, K. E., Lackman, L., Lieberman, H. A., eds. Pharmaceutical dosage forms: parenteral medications, vol. 1, New York: Marcel Dekker, pp. 139–201 (1984).

NCI Investigational Drugs, Pharmaceutical Data, pp 70–72 (NIH publication No. 86–2141, revised March 1986).

Nicolaou, K. C., Riemer, C., Kerr, M. A., Rideout, D., and Wrasidlo, W., Nature vol 364, pp 464–466 (1993).

Pfeifer R. W. and Hale K. N. Precipitation of paclitaxel during infusion by pump, Am J Hosp Pharm 50:2518, 2521 (Dec) 1993.

Rowinsky, E. K and Donebower, R. C. Seminars in Oncol. vol. 20, pp 16–25 (1993).

Sharma, A., and Straubinger, R. M., Pharm Res. vol. 11, 889–896 (1994).

Tarr, B. D., Sambandan, T. G., and Yalkowsky, S. H., Pharm. Res. vol 4, pp 162–165 (1987).

Trissel LA and Bready BB: Turbidimetric assessment of the compatibility of taxol with selected other drugs during simulated Y-site injection, Am J Hosp Pharm 49:1716–1719 (Jul) 1992.

Trissel, L. A., Handbook on injectable drugs, 8th ed. Bethesda, Md.: American Society of Hospital Pharmacists; 1994.

Trissel LA and Martinez J. F. Turbidimetric assessment of the compatibility of taxol with 42 other drugs during simulated Y-site injection, Am J Hosp Pharm 50:300–304 (Feb) 1993.

Waugh W. N., Trissel L. A., and Stella V. J. Stability, compatibility, and plasticizer extraction of taxol (NSC-125973) injection diluted in infusion solutions and stored in various containers, Am J Hosp Pharm 48:1520–1524 (Jul) 1991.

Wiernik, P. H., Strauman, J. J., Engel, S. I., Schwartz, E. L., and Dutcher, J. P. Proc. Am. Soc. Clin Oncol. vol 5, p 32 (1986).

Yalkowsky, S. H., and Valvani, S. C., Drug Intell. Clin. Pharm. vol 11, pp 417–419 (1977).

What is claimed is:

1. A paclitaxel composition comprising:
   (a) paclitaxel at between about 1 mg/mL and about 5 mg/mL;
   (b) surfactant at between about 10% and about 50% (vol/vol); and
   (c) solvent at between about 12% and about 90% (vol/vol).

2. The composition according to claim 1, wherein the surfactant is polysorbate or polyoxyethylated castor oil.

3. The composition according to claim 2, wherein the polyoxyethylated castor oil is at a concentration between about 10% and about 50%.

4. The composition according to claim 3, wherein the polyoxyethylated castor oil concentration is between about 20% and about 30%.

5. The composition according to claim 4, wherein the polyoxyethylated castor oil concentration is about 25%.

6. The composition according to claim 1, wherein the solvent is dehydrated alcohol propylene glycol or polyethylene glycol.

7. The composition according to claim 6, wherein the dehydrated alcohol is ethanol and the concentration is between about 30% and about 85% in the concentrate prior to dilution for administration to a patient.

8. The composition according to claim 7, wherein the alcohol concentration is between about 60% and about 80%.

9. The composition according to claim 8, wherein the alcohol concentration is about 75%.

10. The composition according to claim 1, further comprising a preservative.

11. The composition according to claim 10, wherein the preservative is benzyl alcohol.

12. A paclitaxel composition that includes paclitaxel at between about 0.5 mg/ml and about 1.5 mg/ml, a solvent at between about 12% and about 80% (vol/vol), and a surfactant at between about 5% and about 20% (vol/vol).

13. The composition according to claim 12, wherein the solvent concentration is between about 15% and about 25% and the surfactant concentration is between about 15% and 25%.

14. The composition according to claim 13, wherein the solvent concentration is about 24% and the surfactant concentration is about 8%.

15. The composition according to claim 13, wherein the solvent concentration is about 16% and the surfactant concentration is about 16%.

16. The composition according to claim 12, wherein the solvent is dehydrated alcohol and the surfactant is a polyoxyethylated oil.

17. The composition according to claim 12, further including a diluent.

18. The composition according to claim 12, wherein the diluent is 0.9% sodium chloride or 5% dextrose.

* * * * *

UNITED STATES PATENT AND TRADEMARK OFFICE
CERTIFICATE OF CORRECTION

PATENT NO. : 5,681,846

DATED : October 28, 1997

INVENTOR(S) : Trissel

It is certified that error appears in the above-identified patent and that said Letters Patent is hereby corrected as shown below:

Column 1, line 35, please replace "injection" with --Injection-- (both occurrences); and line 60, please replace "0,115" with --0.115--.

Column 12, line 35, please replace "0,025" with --0.025--.
Claim 6, column 19, line 7, please insert --,-- after "alcohol".

Claim 18, column 20, line 18, please replace "12" with --17--.

Signed and Sealed this

Seventeenth Day of March, 1998

Attest:

BRUCE LEHMAN

Attesting Officer

Commissioner of Patents and Trademarks